(12) United States Patent
Dong et al.

(10) Patent No.: US 6,294,379 B1
(45) Date of Patent: Sep. 25, 2001

(54) EFFICIENT AAV VECTORS

(75) Inventors: Jian-Yun Dong, Mt. Pleasant, SC (US); Yuet Wai Kan, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/256,703

(22) Filed: Feb. 24, 1999

Related U.S. Application Data

(60) Provisional application No. 60/075,980, filed on Feb. 25, 1998.

(51) Int. Cl.⁷ .................. C12N 15/864; C12N 15/12; C07H 21/04
(52) U.S. Cl. ............... 435/320.1; 536/23.1; 536/23.2; 536/23.5; 536/24.1
(58) Field of Search .............. 435/235.1, 320.1, 435/455, 456, 69.1; 536/23.1, 23.2, 23.5, 24.1

(56) References Cited

U.S. PATENT DOCUMENTS

| | | |
|---|---|---|
| 5,587,308 | 12/1996 | Carter et al. . |
| 5,658,776 | 8/1997 | Flotte et al. . |
| 5,866,696 | 2/1999 | Carter et al. . |
| 5,989,540 * | 11/1999 | Carter et al. ............ 424/93.2 |

OTHER PUBLICATIONS

Flotte et al., PNAS, vol. 90, pp. 10613–10617, Nov. 1993.*

Flotte et al. (1996) "A phase I study of an adeno–associated virus–CFTR gene vector in adult CF patients with mild lung disease", *Hum. Gene Ther.* 7:1145–59.

Flotte et al. (1997) "In vivo gene therapy with adeno–associated virus vectors for cystic fibrosis", *Adv. Pharmacol.* 40:85–101.

Flotte et al. (1993) "Expression of the Cystic Fibrosis Transmembrane Conductance Regulator from a Novel Adeno–associated Virus Promoter", *J. Biol. Chem.* 268:3781–3790.

* cited by examiner

*Primary Examiner*—David Guzo
(74) *Attorney, Agent, or Firm*—Townsend & Townsend & Crew LLP

(57) ABSTRACT

The present invention provides improved AAV vectors for delivery of therapeutic nucleic acids. In particular, it provides vectors for delivery of CFTR polynucleotides.

12 Claims, 6 Drawing Sheets

```
  1  AAGAAAATAT ATTTGCATGT CTTTAGTTCT ATGATGACAC AAACCCCGCC
 51  CAGCGTCTTG TCATTGGCGA ATTCGAACAC GCAGATGCAG TCGGGCGGC
101  GCGGTCCCAG GTCCACTTCG CATATTAAGG TGACGCGTGT GGCCTCGAAC
151  ACCGAGCGAC CCTGCAGCGA CCCGCTTAAC AGCGTCAACA GCGTGCCGCA
```

Figure 6

EFFICIENT AAV VECTORS

CROSS REFERENCE TO RELATED APPLICATIONS

This application claims priority to U.S. Ser. No. 60/075,980, filed Feb. 25, 1998 which is incorporated herein by reference.

STATEMENT AS TO RIGHTS TO INVENTIONS MADE UNDER FEDERALLY SPONSORED RESEARCH AND DEVELOPMENT

This invention was made with Government support under Grant No. DK/HL46177, awarded by the National Institutes of Health.

BACKGROUND OF THE INVENTION

The transfer of genetic material into cells in mammals is of increasing commercial importance. For instance, gene therapy procedures are used to correct acquired and inherited genetic defects, cancer, and viral infection. The ability to express artificial genes in humans facilitates the prevention and/or cure of many important human diseases, including many diseases which are not amenable to treatment by other therapies.

One of the most common fatal genetic diseases in humans is cystic fibrosis (CF). Cystic fibrosis (CF), a spectrum of exocrine tissue dysfunction,.which eventually leads to respiratory failure and death results from a mutation of the cystic fibrosis transmembrane conductance regulator (CFTR) gene. The CFTR gene has now been localized to chromosome 7q31, and cloned. A 3 bp deletion, resulting in the loss of a phenylalanine residue at amino acid position 508, is present in approximately 70% of CF chromosomes, but is not seen on normal chromosomes. The other 30% of CF mutations are heterogenous and include deletion, missense, and splice-site mutations.

The major mortality in CF is from pulmonary disease. There is no cure for CF. Current treatments for CF include antibiotics to treat bacteria (pseudomonas) infection, and respiratory physical therapies to remove the mucus blocking the airways of the patients. A recent therapy for CF is recombinant Dnase ("THERAZYME") developed by Genentech to reduce the thickness of the mucus. The drug is expensive and requires daily dose inhalations and combination with physical therapy to remove the mucus from the lungs of the patients. It does not treat the basic defect of CF, that is, the malfunction in chloride transport.

Gene therapy has the potential to provide long term relief in patients by expressing the normal gene in the diseased cells to form normal chloride channel function. Transfection of even a single normal copy of a functional CFTR gene abolishes the CF secretory defect in CF cell lines, an observation which supports the feasibility of gene therapy for CF. see, e.g., Capelen et al. Nature Medicine 1(1): 39 (1995), McLachlan et al., Gene Ther. 3(12): 1113–23 (1996).

Several approaches for introducing functional new genetic material into cells in vivo have been used. These include liposome based gene delivery (Debs and Zhu (1993) WO 93/24640; Mannino and Gould-Fogerite (1988) Bio-Techniques 6(7): 682–691; Rose U.S. Pat. No. 5,279,833; Brigham (1991) WO 91/06309; and Felgner et al. (1987) Proc. Natl. Acad. Sci. USA 84: 7413–7414) and replication-defective retroviral vectors harboring a therapeutic polynucleotide sequence as part of the retroviral genome (see, e.g., Miller et al. (1990) Mol. Cell. Biol. 10:4239 (1990); Kolberg (1992) J. NIH Res. 4:43, and Cometta et al. Hum. Gene Ther. 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof See, e.g., Buchscher et al. (1992) J. Virol. 66(5) 2731–2739; Johann et al. (1992) J. Virol. 66 (5):1635–1640 (1992); Sommerfelt et al., (1990) Virol. 176:58–59; Wilson et al. (1989) J. Virol. 63:2374–2378; Miller et al., J. Virol. 65:2220–2224 (1991); Wong-Staal et al., PCT/IJS94/05700, and Rosenburg and Fauci (1993) in Fundamental Immunology, Third Edition Paul (ed) Raven Press, Ltd., New York and the references therein, and Yu et al., Gene Therapy (1994) supra). For a review of gene therapy procedures, see Anderson, Science (1992) 256:808–813; Nabel and Felgner (1993) TIBTECH 11: 211–217; Mitani and Caskey (1993) TIBTECH 11: 162–166; Mulligan (1993) Science 926–932; Dillon (1993) TIBTECH 11: 167–175; Miller (1992) Nature 357: 455–460; Van Brunt (1988) Biotechnology 6(10): 1149–1154; Vigne (1995) Restorative Neurology and Neuroscience 8: 35–36; Kremer and Perricaudet (1995) British Medical Bulletin 51(1) 31–44; Haddada et al. (1995) in Current Topics in Microbiology and Immunology Doerfler and Böhm (eds) Springer-Verlag, Heidelberg Germany; and Yu et al., Gene Therapy (1994) 1:13–26.

AAV-based vectors are used to transduce cells with target nucleic acids, e.g., in the in vitro production of nucleic acids and peptides, and in in vivo and ex vivo gene therapy procedures. See, West et al. (1987) Virology 160:38–47; Carter et al. (1989) U.S. Pat. No. 4,797,368; Carter et al. WO 93/24641 (1993); Kotin (1994) Human Gene Therapy 5:793–801; Muzyczka (1994) J. Clin. Invst. 94:1351 and Samulski (supra) for an overview of AAV vectors. Construction of recombinant AAV vectors are described in a number of publications, including Lebkowski, U.S. Pat. No. 5,173,414; Tratschin et al. (1985) Mol. Cell. Biol. 5(11): 3251–3260; Tratschin, et al. (1984) Mol. Cell. Biol., 4:2072–2081; Hermonat and Muzyczka (1984) Proc. Natl. Acad. Sci. USA, 81:6466–6470; McLaughlin et al. (1988) and Samulski et al. (1989) J. Virol., 63:03822–3828. Cell lines that can be transduced by AAV include those described in Lebkowski et al. (1988) Mol. Cell. Biol., 8:3988–3996.

AAV has also been used to deliver CFTR genes in vivo Flotte, T. et al., Hum. Gene Ther. 7:1145–59 (1996); Flotte, T. R. et al., Proc. Natl. Acad. Sci. USA 90:10613–7 (1993); Flotte, T. R. et al. J. Biol. Chem. 268:3781–90 (1993); and Flotte, T. R. et al., Adv. Pharmacol. 40:85–101 (1997).

Currently, three vector systems are being tested to deliver CFTR gene into airway epithelial cells, a non-viral vector (liposomes), and two viral vectors, adenovirus and AAV. Recent clinical trials have demonstrated that the AAV vector can efficiently and persistently transfer the CFTR gene into the airway epithelimn of patients without any adverse effects (see, Flotte, T. et al., Hum. Gene Ther. supra). In spite of these advantages, previous AAV vectors do not express sufficient levels of CFTR. Because of size constraints, an effective promoter cannot be accommodated with the CFTR gene. This limits the clinical efficacy of the vector for gene therapy of cystic fibrosis. The present invention addresses these and other needs.

SUMMARY OF THE INVENTION

The present invention provides AAV vectors which lack AAV nucleic acids which are nonessential for vector construction. The vectors also comprise a transcription cassette containing a nucleic acid of interest, and a pair of AAV ITR sequences. The nucleic acid of interest can be any therapeutic nucleic acid. An exemplary therapeutic nucleic acid is a CFTR polynucleotide, such as the truncated CFTR polynucleotide as shown in FIG. 2.

The invention also provides expression cassettes comprising a truncated CFTR polynucleotide encoding a functional CFTR polypeptide. An exemplary CFTR polynucleotide of the invention is shown in SEQ ID NO: 1. The expression cassettes also comprise promoters, preferably truncated promoters. Examples of truncated promoters include an AAV P5 promoter of about 150 bp, an HSV TK promoter of about 100 bp, or an SV40 early promoter of about 200 bp. The expression cassettes will also include polyadenylation signals. A sequence is a 67 bp polyadenylation sequence from the TK gene of HSV. The expression cassettes may be incorporated into any vector suitable for delivery of desired nucleic acids to cells. The AAV vectors of the invention are preferred.

Definitions

An "AAV ITR sequence" refers to the sequences which comprise the palindromic terminal repeats at the 3' and 5' ends of the AAV genome. Typically, the repeats are about 150 nucleotides in length. The AAV ITR regions provide sequences for packaging the AAV provirus (i.e., the AAV genome) into the AAV viral capsid. The ITR regions also form secondary structures which act as self-primers for AAV replication. Samulski (1993) Current Opinion in Genetic and Development 3:74–80 describes AAV ITR sequences and structures.

As used herein an AAV vector which "lacks non-essential AAV nucleic acids" is an AAV vector which includes only the two 145 nucleotide ITR sequences and less than about 10 nucleotides from the AAV genome that are not part of the ITR (i.e., non-essential AAV sequences). The vectors preferably contain less than about 5 nucleotides and most preferably no nucleotides of non-essential AAV sequence.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising CFTR nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

BRIEF DESCRIPTION OF THE DRAWINGS

FIG. 6 shows the sequence (SEQ ID NO:6) of an HSV-TK promoter of the invention.

FIG. 7A shows absence of activities in these cells when not infected with the virus vector (no virus). After infection (indicated by p5D4.1C2), activities could be measured, and typical of chloride channel, could be stimulated by Forskolin, and inhibited by the chemical, diphenyl carboxylate (DPC). FIG. 7B indicates the voltage/current relationship of the cells when increasing voltage was applied after infection (Control), with addition of Forskolin, and DPC. FIG. 7C plots the results in B in graphic form. Open circles: Control; closed circles: Forskolin; inverted triangles: DPC.

DESCRIPTION OF THE PREFERRED EMBODIMENT

Figure 1:
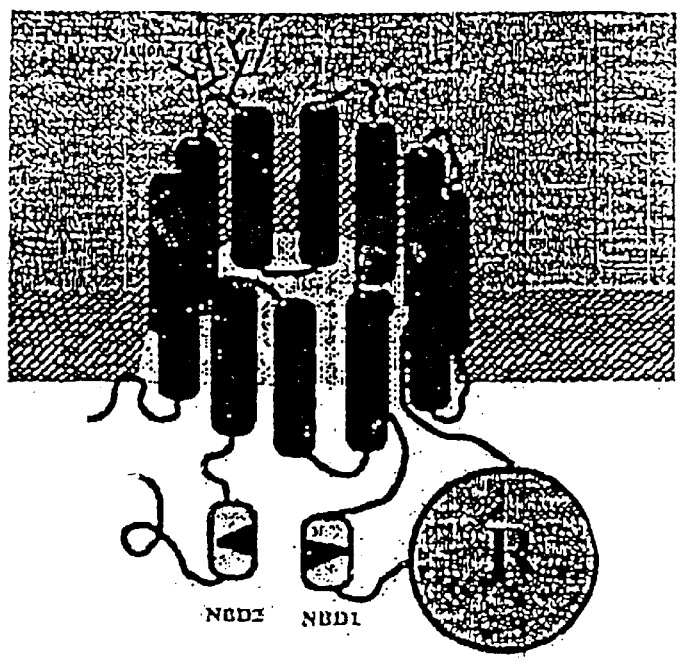
FIG. 1 is a schematic diagram of CFTR gene. It comprises the N-terminal region and a C-terminal region (cytoplasmic tail), as indicated by the thick gray lines, 12 transmembrane regions (vertical columns), a regulatory domain (circle) and two nucleotide binding domains (NBD1 and NBD2).

Unless defined otherwise, all technical and scientific terms used herein have the same meaning as commonly understood by one of ordinary skill in the art to which this invention belongs. Singleton et al. (1994) Dictionary of Microbiology and Molecular Biology, second edition, John Wiley and Sons (New York); Walker (ed) (1988) The Cambridge Dictionary of Science and Technology, The press syndicate of the University of Cambridge, N.Y.; and Hale and Marham (1991) The Harper Collins Dictionary of Biology Harper Perennial, N.Y. provide one of skill with a general dictionary of many of the terms used in this invention. Paul (1993) Fundamental Immunology, Third Edition Raven Press, New York, N.Y. and the references cited therein provide one of skill with a general overview of the ordinary meaning of many of the virally or immunologically related terms herein. Methods and materials similar or equivalent to those described herein can be used in the practice or testing of the present invention.

The present invention provides improved AAV vectors for delivering large expression cassettes to cells of interest. In particular, the AAV vectors of the invention lack non-essential AAV sequences and includes only the ITR sequences necessary for essential functions of the AAV vector, thus allowing for increased expression cassette size in the vectors.

For example, the invention provides an efficient AAV-CFTR vector for gene transfer in cystic fibrosis. This vector is over ten times more efficient than prior art CFTR vectors. Because the coding region of the CFTR cDNA is so large that an effective promoter cannot be accommodated, an expression cassette comprising a truncated CFTR gene expressed from an efficient promoter and a minimal poly A site was constructed. The vector itself contains only the ITR sequences and has the maximal packaging capacity for foreign DNA. The CFTR gene contains deletions in regions that are not essential for its function. The truncated CFTR retained a wild type like activity. The polyadenylation site is selected to be as small as possible. For example, the polyadenylation sited can be isolated from the HSV TK polyA which contains only the conserved sequence and a poly purine tracts, and is 65 bp in size. The short promoter can be P5 of AAV, TK, truncated SV40 or any promoters under 250 bp in size. The total size of the vector is within the optimal range of packaging size of AAV that allows production of high titers of AAV particles for gene transfer.

Thus, the major features of the CFTR AAV vectors of the invention are: (1) The vector contains only the essential inverted terminal repeat (ITR) sequences of AAV to spare all the packaging capacity for therapeutic gene sequences; (2) The CFTR mini-gene contains deletions in non-essential regions, and encodes a smaller protein that has a similar function as the wild type; (3) The AAV vector contains a promoter and (4) a truncated poly A signal to express the CFTR gene at high levels. The level of CFTR expression from this AAV vector is over 10 times higher than the AAV vector in which the CFTR gene is driven by the ITR of the AAV.

AAV-based vectors are used to transduce cells with nucleic acids of interest e.g., in the in vitro production of nucleic acids and peptides, and in in vivo and ex vivo gene therapy procedures. See, West et al. (1987) Virology 160:38–47; Carter et al. (1989) U.S. Pat. No. 4,797,368; Carter et al. WO 93/24641 (1993); Kotin (1994) Human Gene Therapy 5:793–801; and Muzyczka (1994) J. Clin. Invst. 94:1351. Samulski (1993) Current Opinion in Genetic and Development 3:74–80 and the references cited therein provides an overview of the AAV life cycle.

Recombinant AAV vectors deliver foreign nucleic acids to a wide range of mammalian cells (Hermonat & Muzycka (1984) Proc Natl Acad Sci USA 81:6466–6470; Tratschin et al. (1985) Mol Cell Biol 5:3251–3260), integrate into the host chromosome (Mclaughlin et al. (1988) J Virol 62: 1963–1973), and show stable expression of the transgene in cell and animal models (Flotte et al. (1993) Proc Natl Acad Sci USA 90:10613–10617). Moreover, unlike retroviral vectors, AAV vectors are able to infect non-dividing cells (Podsakoff et al. (1994) J Virol 68:5656–66; Flotte et al. (1994) Am. J. Respir. Cell Mol. Biol. 11:517–521). Further advantages of AAV vectors include the lack of an intrinsic strong promoter, thus avoiding possible activation of downstream cellular sequences, and their naked icosohedral capsid structure, which renders them stable and easy to concentrate by common laboratory techniques.

AAV vectors have several properties which make them preferred gene delivery systems in clinical settings. They have no known mode of pathogenesis and 80% of people in the United States are currently seropositive for AAV (Blacklow et al. (1971) J Natl Cancer Inst 40:319–327; Blacklow et al. (1971) Am J Epidemiol 94:359–366). Because AAV vectors have little or no endogenous promoter activity, specific promoters may be used, depending on target cell type. AAV vectors can be purified and concentrated so that multiplicities of infection exceeding 1.0 can be used in transduction experiments. This allows virtually 100% of the target cells in a culture to be transduced, eliminating the need for selection of transduced cells.

The vectors of the invention can be used to deliver a "transcription cassette" into an appropriate cellular target. A transcription cassette is a nucleic acid subsequence encoding a nucleic acid which is transcribed. To facilitate transcription, nucleic acid elements such as promoters and enhancers and transcriptional termination sequences are typically included in the transcription cassette. Where the transcribed nucleic acid is translated by cellular machinery into a protein, the transcription cassette can also be referred an "expression cassette". An expression cassette typically includes translational start and stop sites, and polyadenylation signals.

The only essential sequences required for an AAV vector are the ITR sequences of AAV. As explained in detail below, AAV vectors that have maximal packaging capacity are provided by the invention.

EXAMPLES

Example 1

This example describes the production of CFTR AAV vectors of the invention. The AAV vectors containing the shortened CFTR genese were constructed as described in Zhang et al. *Proc. Nati. Acad. Sci. U.S.A.* 95:10158–10163 (1998).

Briefly, the CFTR cCNA was inserted into pP5TK65, which contains the P5 promoter, followed by a 65 bp, truncated poly A signal from the TK gene of herpes simplex virus. The transcriptional cassette containing the CFTR gene then was inserted into an AAV vector, pAV53. The two ITR sequences of pAV53 and part of the linker sequences were 302 bp in length. For comparing the levels of expression, a minimal CFTR cDNA containing the entire cosing sequence was cloning into pAV53 with only the TK poly A signal. In this construct, the CFTR cDNA is expressed from the putative promoter in the ITR sequence. Transducing AAV virions were prepared as described in Fan et al. *Hum. Gene Ther*. 8:89–98 (1997).

The AAV vector

The AAV vector with the maximal packaging capacity should contain only the two ITR (145 nt) sequences. Such vectors have not been available for three reasons: (1) The ITR sequences contain repeated sequences that have a strong tendency toward forming stable secondary structures. This makes it difficult to clone the ITR sequences alone without including surrounding sequences. (2) The formation of secondary structure makes it difficult to amplify the full length ITR with standard PCR techniques. (3) When closely located, the two ITR sequences are unstable in bacteria in which vector DNAs are propagated. Propagation of such vector in *E. coli* frequently results in deletion of one ITR sequence and the cloning site.

To overcome these hurdles, a strategy was developed to PCR-amplify the ITR sequences with two overlapping oligos that cover the entire ITR region. The PCR products were cloned into a plasmid, pSP73 (Promega). Sequence analysis of the amplified ITR sequences demonstrated that the amplified fragments were a population of ITR sequences containing variable deletions in the repeated regions. Different from the results of standard PCR-amplification, the majority of the PCR products contained only small deletions and one full-length ITR was identified in every five to seven sequenced clones. Using standard PCR with two small oligo-primers, the PCR products were a population of molecules with various and extensive deletions. It was not possible to clone out any full-length ITR in spite of repeated attempts.

The left-hand ITR sequence in a flip conformation was synthesized with a pair of overlapping DNA oligomers. The 5'-oligomer (L5ITR oligo) contains bases 1–76 of AAV DNA sequence. The 3'-oligomer (L3ITR) contained the ITR sequence bases 50–145 and the sequence of an Xba 1 site. The right-hand ITR sequence in a flop conformation was synthesized with a pair of similar oligomers containing sequences of the right-hand ITR. The 5'-oligomer (R5ITR) contained sequence of an Xho I site and the AAV sequence of bases 4535–4611. The 3'-oligomer contained the AAV sequence of bases 4585–4680. The oligomers in each pair were mixed in equimolar amounts and annealed at 51 degrees C in a PCR machine followed by 20 cycles of PCR extension reactions. The last anneal reaction was carried out with a 10 minute temperature slope from 90 degrees C to 40 degrees C. The annealed products were subjected to electrophoresis on an 8% acrylamide gel. The bands in the size range of double-stranded ITR (160 bp including the restriction site and additional sequences to allow digestion at the site) were isolated. The purified left or right-hand ITR DNA fragment was digested with Xba I or Xho I, respectively, and ligated into a plasmid vector pSP73.

The left-hand ITR fragment was cloned into the Xba I and the blunt-ended NdeI sites in the pSP73 vector. Seven clones of the ITRs were sequences and the clones containing the correct ITR sequence were designated as pSPITR-L. In a second step, an irrelevant spacer sequence from bacterial DNA was cloned into pSPITR-L resulting in pITR-LS. The right-hand ITR sequence was then cloned into the Hpa I and Xho I sites of pITR-LS. After confirming the correct sequence of the right-hand ITR, the vector was designated as pAV53. This vector contains only the left-hand and the right-hand ITR sequences of AAV and therefore should therefore provide the maximal packaging capacity for the gene of interest.

The CFTR Gene

The coding sequence of a wild type CFTR gene has been cloned and is 4.45 kb in length (see, EPO Publication Number 0 446 017 A1, Goodfellow, P., *Nature* (1989) 341:102–103; Rommens, et al., *Science* (1989) 245:1059–1054 and Riordan et al. *Science* (1989) 245:1066–1073). To efficiently express the mini-gene it requires a minimum 20 bp untranslated region which contains a Kozak sequence at the 5'-end of the gene. The CFTR mini-gene encodes a protein that is predicted to have an N-terminal loop region, 12 transmembrane domains, two nucleotide binding domains, a regulatory (R) domain and a cytoplasmic tail region. The structure of the CFTR protein is schematically diagrammed in FIG. 1 and the sequence of the cDNA and protein are show in SEQ ID NO: 1 and SEQ ID NO: 2, respectively.

Deletion analysis of CFTR gene can be used to reduce the size of the coding region while maintaining its protein function. For example, a preferred strategy is to delete the regions that have no or few naturally occurring missense point mutations. The lack of missense mutations suggests that these mutations may not cause diseases because they do not affect the function of the CFTR. Means for testing function of a truncated CFTR polynucleotide are known (see, e.g., Rich et al. Receptors and Channels 1:221–32 (1993) and Xie et al. Biophys. J. 71:3148–56 (1996).

As explained below, 16 deletions ranging from 51 to 360 bp at the N-terminal, cytoplasmic tail region, transmembrane domains, the loop regions between transmembrane domains, and the R domain have been made in the gene. The regions into which deletions were introduced are schematically diagrammed in FIG. 2. Two non-essential regions have been identified using this deletional screening approach. The first region is the cytoplasmic domain between nucleotide 4441 and 4572 (C-deletion). The second is a stretch of sequences between nucleotide 2521 and 2646 (R-deletion) that encode the flexible region of the R domain. It was also found that combining the C deletion and R deletion generated an even smaller CFTR protein with wild type-like CFTR activity.

Reduction in the Coding Region of CFTR cDNA.

The CFTR cDNA is >7.2 kb, of which the sequence encoding for the wild-type CFTR protein is 4.45 kb. However, to express efficiently the mini-gene, it requires some untranslated regions. Hence, in our construct, 30-bp containing the Kozak sequences were included upstream of the AUG codon, and 65 bp containing the poly(A)signal were included downstream of the stop codon of the CFTR cDNA. To reduce further size of the coding region, we targeted deletions into regions that have probability of containing nonessential sequences. Deletions were introduced into the CFTR cDNA by using a two-step PCR amplification. The first 5'-primer contained sequences flanking the regions to be deleted. The 3'-primer spanned or passed a unique restriction site that was to be used for cloning the amplified fragment. After the first amplification, a second 5'-primer that spanned a second restriction at the 5'-end of the fragment was used for the second amplification. The final amplified fragments were sequenced and cloned into the corresponding region of the CFTR in a plasmid, pBQ4.5, which contained the entire coding region of CFTR and the minimal untranslated regions. We made 20 deletions ranging from 51 to 360 bp at the N-terminal, the cytoplasmic tail region, the transmembrane domains, the loop regions between transmembrane domains, and the R domain. The regions into which we have introduced deletions are listed in Table 1.

TABLE 1

Deletions in the CFTR mini gene

| Constructs* | Regions deleted† | Nucleotides deleted‡ | as removed, n |
|---|---|---|---|
| ΔC1 | C | 4,503–4,725 | 23 |
| ΔC2 | C | 4,441–4,725 | 44 |
| ΔC3 | C | 4,357–4,725 | 72 |
| ΔC4 | C | 4,314–4,725 | 86 |
| ΔN1 | N | 73–184 | 17 |
| ΔN2 | N | 73–241 | 36 |
| ΔN3 | N | 73–295 | 54 |
| D1 | N | 247–372 | 42 |
| ΔT2 | N | 256–646 | 130 |
| ΔT4 | N | 256–922 | 222 |
| ΔT6 | N | 298–1,342 | 348 |
| D2 | LEE Declaration Exhibit | 886–981 | 32 |
| D3 | LEE Declaration Exhibit | 1,225–1,351 | 42 |
| D4,1 | R | 2,521–2,647 | 42 |
| D4,2 | R | 2,401–2,647 | 82 |
| D4,3 | R | 2,281–2,647 | 122 |
| D5 | T | 3,058–3,244 | 62 |
| D6 | LEE Declaration Exhibit | 3,601–3,727 | 42 |
| D4.1C1 | LC | 2,521–2,647/ 4,503–4,725 | 65 |
| D4,1C2 | LC | 2,521–2,647/ 4,441–4,725 | 86 |

*AC1, AC2, AC3 and AC4 contain stop codons from the primers that are used to make the deletions. AN1, AN2 and AN3 have the Kozak sequences from the primers used.
†C,N,L or R indicates C-terminal, N-terminal, loop region and regulation domain, respectively.
‡The numbers of nucleotides deleted in C1–4 and N1–3 deletions include nontranslated regions. In the wild-type cfrr cDNA, the start codon and the stop codon are located at nt 133 and nt 4,573, respectively.

Functional Assays of the Shortened CFTR.

Initial screening for functional shortened CFTR was carried out by using an established $^{125}$I-efflux assay as described by Ohrui et al. *J. Appl. Physiol.* 78:1197–1202 (1995). In brief, 293 cells were transfected stably with a plasmid containing each of the shortened CFTR mini-cDNA. The cells grown on 18-mm cover glass (Fisher) in 24-well plates (Nunc) were incubated in culture medium containing Na$^{125}$I (20 μCi/ml) for 1 hr. Incubation medium was removed, and the cells were washed twice briefly (10 s) with Kreb's buffer described in Ohrui et al. to remove extracellular Na$^{125}$I. Medium (1 ml) then was added to the cells, removed, and replaced with fresh medium at 1-min intervals. Cells then were stimulated with 10 mM forskolin, 1 mM isobutylmethylxanthine, and 200 mM 8-(4-chlorophenylthio)-CAMP with additional medium changes and incubations. Cells were lysed in 0.1 N NaOH (1 ml), and radioactivity in cell and efflux samples was measured with a γ counter. The effluxes were expressed as fractional rate of loss =[(A−B)/A]×100 where A is the number of counts in the cells at the start of a 1-min efflux period and B is the counts at the end.

Whole-cell patch-clamp was used to analyze the levels of CFTR expression from the AAV vectors in transduced HeLa cells. The characteristics of the shortened CFTR genes also were analyzed with single-channel patch-clamp, under cell-attached or -detached conditions as described in detail previously in Fischer et al. *J. Physiol.* 489:745–754 (1995). In brief, cells were placed in an open, constantly perfused chamber (37° C.). Solutions were designed to measure chloride currents only. In the cell-attached mode, bath and pipette were filled with a solution containing: 145 mM N-methyl-d-glucamine chloride (NMDGCl), 1.7 mM CaCl$_2$, 1 mM MgCl, 10 mM Hepes, and 10 mM glucose (pH 7.3).

Single-channel conductance was determined by clamping voltage from −80 to 80 mV in 20-mV steps. For calculation of open probabilities, the apparent number of channels per patch was estimated by dividing the maximal current with the single-channel current. In the whole cell mode, pipette solution contained 145 mM NMDGCl, 0.1 mM EGTA, 1 mM MgCl$_2$, 10 mM Hepes, 10 mM glucose, and 5 mM MGATP (pH 7.3). For continuous whole cell recordings, membrane potential was clamped to −60 mV. Current-voltage relations were generated from superimposed 200-ms voltage steps from −20 to 100 mV in 20-mV steps. Cells were stimulated with 10 μM forskolin (Calbiochem) in the bath solution. Subunit of catalytic protein kinase A (Promega) was used at 50 units/ml.

20 deletions were made, ranging from 51 to 360 bp at the N-terminal, cytoplasmic tail region, transmembrane domains, the loop regions between transmembrane domains, and the R domain. The regions where deletions were introduced are diagrammed schematically in FIG. 2. The function of these modified CFTR genes was analyzed by using $^{125}$I efflux of cells stably transfected with each CFTR gene containing deletions. We identified two nonessential regions by using this deletional screening approach. The first region is the cytoplasmic domain between nucleotides 4,441 and 4,572 (C-deletion) as defined by three deletional mutants, ΔC1, ΔC2 and ΔC3, which contain progressive deletions from the C terminus of the CFTR protein (see Table 1 for details). ΔC1 and ΔC2, which removed 23 and 44 aa residues, did not affect CFTR function as determined by the $^{125}$I efflux assays. The second region is a stretch of sequence between nucleotide 2,521 and 2,646 (R-deletion) that encodes the flexible region of the R domain. This region also was defined by the three deletion mutants, D4.1, D4.2, and D4.3, which contain deletions progressively extending from the flexible region into the globular region of the R domain. D4.1, which removed 40 aa residues demonstrated a wild type-like Cl$^-$ channel activity. D4.2, with a 80-aa deletion, showed a delayed activation response to forskolin stimulation, and D4.3, with a 120-aa deletion that extended into the globular region of the R-domain, did not show a significant amount Cl$^-$ channel activity. Combining the C deletion (ΔC2) and R deletion (D4.1) resulted in a cDNA (D4.1 C2) encoding an even smaller CFTR protein with wild-type CFTR activity.

Efficient Transfer of Shortened CFTR Gene with AAV Vectors.

To evaluate the AAV-mediated transduction of the short CFTR genes, we analyzed CFTR function with patch-clamp techniques. We infected HeLa cells that do not express CFTR with equal volumes of viral lysate containing AAVp5ΔC2 or AAVp5D4.1C2 (an AAV vector containing ΔC2 or D4.1C2 driven by a P5 promotor) and analyzed CFTR function with cell-attached and excised patch-clamp recordings. Treatment with protein kinase (PKA) readily activated current carried by multiple channels present in a single patch. Current-voltage (I/V) protocol applied during PKA treatment and I/V relations showed that the current in the excised mode was time-and voltage-independent The total activated conductance in the patch was 64 pS, which is equivalent to ≈16–20 Cl channels (assuming an open probability of 0.5 and 6–8 pS for single CFTR). This indicated high levels of CFTR expression from the AAV vector.

With AAV-mediated transduction, we also were able to investigate the single-channel properties of the shortened CFTR gene. In cells infected with AAVp5ΔC2, cell-atched recordings showed a linear Cl$^-$ channel with a conductance of 6.4±0.16 pS (n=5). Patch-clamp recording of cells infected with AAVp5D4.1C2 showed a significantly larger Cl⁻ channel with a conductance of 8.7±0.6 pS (n=6). I/V relation curves showed both channels to be time- and voltage-independent. Of interest, both ΔC2 and D4.1C2 exhibited very long open bursts and long closed times. During the stimulation, the average open probability was >0.5, comparable to the wild-type CFTR. These recordings confirmed that the CFTR deletion mutants form functional and cAMP/PKA-regulated Cl channels. Their biophysical characteristics (i.e., time- and voltage-independent activation and open probability) were not affected by the deletions, and their conductance was in the reported range of wild-type CFTR. The notable difference of the shortened CFTR compared with wtCFTR was the longer open and closed times.

Shorter CFTR Genes Are More Efficient in Transferring CFTR Function into Target Cells.

We further analyzed the efficiencies of the different AAV/CFTR vectors in transferring the CFTR gene into target cells. The levels of transferred CFTR function were assayed with whole-cell patch-clamp measurements. This technique is quantitative because it compares the levels of CFTR expression in cells by measuring the amount of the CL⁻ current conducted. In this experiment, cells were infected with equal amounts of AAV stocks produced under identical conditions. AAV-CFTR, the vector containing a full length CFTR gene controlled by the ITR, was included for comparison. Whole-cell patch-clamp recordings of cells transduced with AAV-CFTR (4,837 bp) AAVp5ΔC2 (4,853 bp), or AAVp54.1C2 (4727 bp) are shown. A strong forskolin-induced CL⁻ current was detected in cells transduced with AAVp5ΔC2 but not in cells transduced with AAV-CFTR that do not contain a heterologous promoter although they are similar in length. An even stronger forskolin-induced Cl⁻ current was recorded in cells transduced with AAVp5D4.1C2, indicating that more efficient transduction of CFTR gene by this shorter vector resulted in the expression of more CFTR channels. Both ΔC2 and D4.1C2 are driven by the same P5 promoter, so the higher level expression of AAVp5D4.1C2 is probably caused by the more efficient packaging into virions of this vector, which is shorter by 126 bp. This is consistent with our previous observations that packaging efficiency is affected greatly by vector size when it is close to the packaging limit. I/V protocol and current-voltage relation showed the CFTR-typical time and voltage independence of currents typical of CFTR and greater conductance mediated by the shorter CFTR genes.

Figure 7:
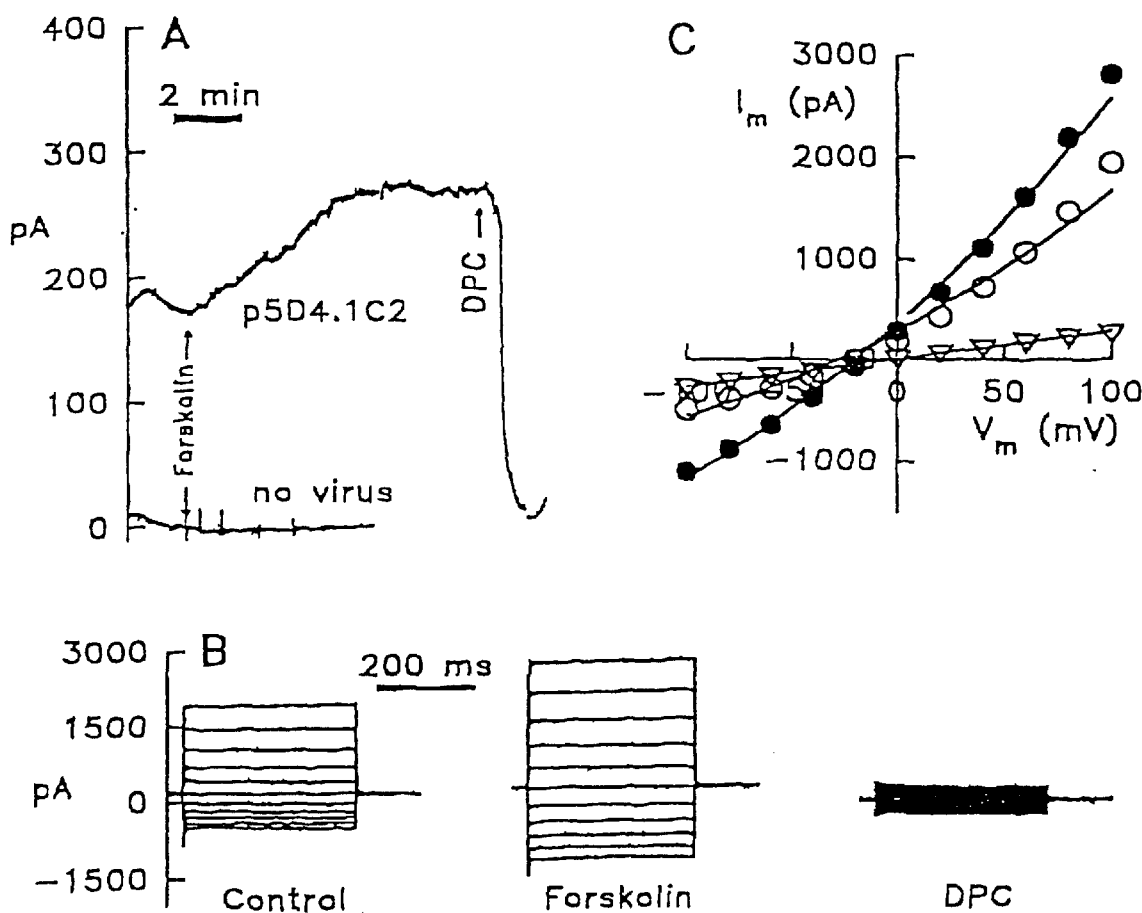
FIGS. 7A–C shows the results of patch clamp studies of AF508 cells infected with AAVp5D4.1C2 (the AAV vector carrying the double deletions in the CFTR cDNA).

FIG. 7 shows the results of patch clamp studies on ΔF508 epithelial cells transduced with AAVp5D4.1C2, an AAV vector carrying a double deletion in the CFTR cDNA.

The Poly A Site

Figure 4:
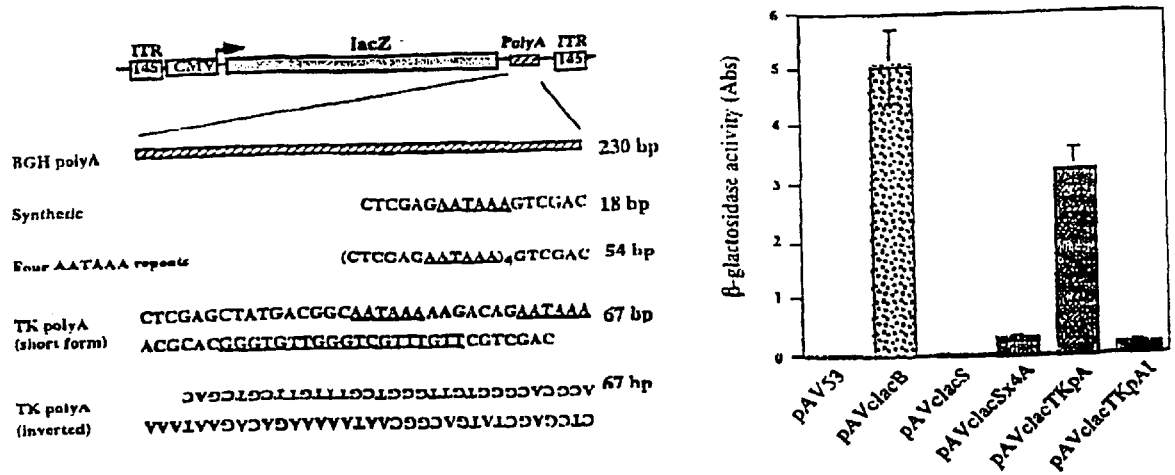
FIG. 4 shows the short polyadenylation signals used in the vectors of the invention. The activities of different poly A signals were analyzed with a quantitative x-gal assay. The sequences of different poly A are shown in the left panel (SEQ ID NOS:3–5). The activities of the poly A are shown in the graph on the right. The 67-bp-TK poly A has the highest activity among the short poly A sequences.

Most of the natural polyadenylation sites are larger than 100 bp in size. To reduce the size of a poly A site, the poly A site of the TK gene of Herpes simplex virus (HSV) was truncated to 67 bp (FIG. 4). Smaller truncated polyA sequences are also functional with a reduced activity. Larger then 67 bp did not significantly increase the polyadenylation activities. Therefore the 67 bp-TK polyA was incorporated into the AAV vector for the CFTR gene expression. However, polyA sequences with slight variation in the sequence are also functional. This will also include synthetic poly A sequence that contains the conserved poly A sequence (AATAAA) and the poly purine tract (GGGTGTTGGGTCGTTTGTT) SEQ ID NO:7.

The Promoters

Figure 5:
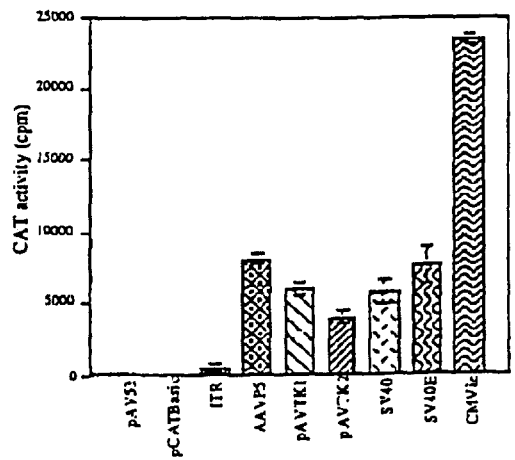
FIG. 5 is a comparison of promoter activities using CAT gene, pAV53: empty vector; pCATBasic; no promoter; ITR driven by AAV ITR; pAVTK1:ITR+100 bp TK promoter; pAVTK2; ITR+92 bpTK promoter; SV40; SV40 promoter (200 bp) SV4OE; early promoter with enhancer, CMVie:CMV immediate-early promoter.

We have reduced the sizes of different promoters including AAV-P5, HSV-TK, and SV40ic promoters. The levels of transcriptional activities of these promoters were compared with ITR and CMVie (a strong promoter, 800 bp) using CAT gene as an indicator (FIG. 5). The size of the AAV P5 promoter has been reduced to 150 bp (consisting of about nucleotide 146 to about nucleotide 295 of the AAV genome), TK promoter has been reduced to 100 bp (consisting of about nucleotide 51 to about 149 as shown in FIG. 6) and the SV40ie promoter has been reduced to 200 bp consisting of about nucleotide 5096 through the circular junction to about nucleotide 54 of the SV40 genome. The general strategy of reducing the size of promoters by truncation and deletions in the non-essential regions can also be applied to other transcriptional elements, such as elongation factor promoter, to generate short forms of functional promoters.

The vectors of the invention can be used for gene therapy of cystic fibrosis. The AAV-CFTR vector will be packaged into AAV particles in a GMP facility. These particles will be purified and concentrated using standard methods. Purified particles can be inhaled, or instilled into the airways of patients. The virions will enter and delivery the CFTR gene into the airway epithelial cells. The CFTR gene carried by the vector will persist in the airways and provide therapeutic effects for the patients.

Example 2

This example shows expression of two halves of a CFTR form a functional Cl-channel.

Figure 8:
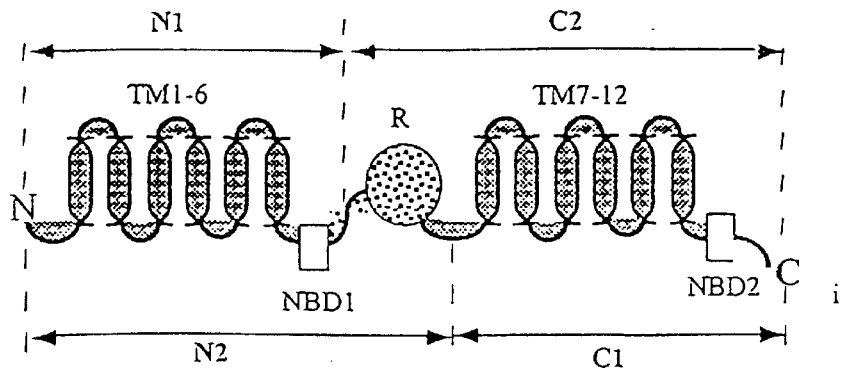
FIG. 8 shows regions that are included in each half-CFTR construct, C1, C2 N1 and N2. Each construct contains one symmetrical half of CFTR. R-domain is included in C2 or N2.
Figure 9:
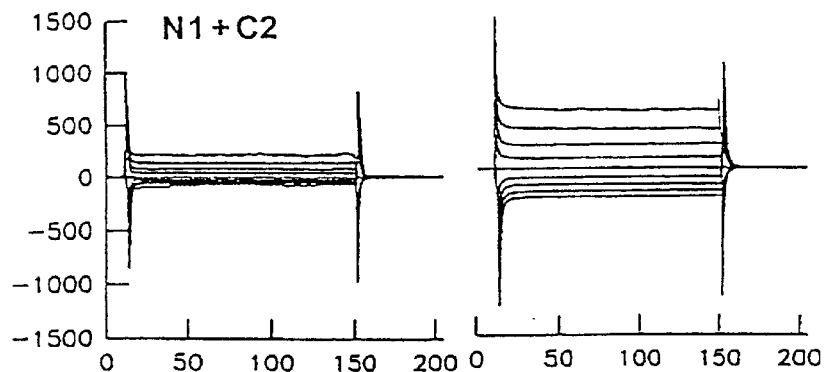
FIG. 9 shows Recording of current-voltage relation of cells transduced with two halves of the CFTR molecule, N1+C2. The current voltage protocols were recorded before (left graph) and after (middle graph) forskolin-stimulation of the cells. The difference (after—before) is plotted in the right hand IV plot. The points are the current differences and the line is the best fit of a GHK equation. The forskolin-stimulated permeability values (stimulated minus basal levels) generated by N1+C2 were between 8.08–11.2 ($10^{-15}$1/S), demonstrating high levels of CFTR activity. Cells transduced N1, C2 alone produced basal C1 permeability but cannot be stimulated (not shown).

The predicated structure of CFTR molecule is symmetrical. It can be artificially divided into two halves, the first contains the transmembrane region (TM) 1–6 and the first nucleotide binding domain (NBD1) and the second contains the TM 7–12 and NBD2. The two halves are separated by a large globular R-domain. It has been suggested that a complete CFTR protein may be formed if each half of the CFTR is expressed separately in the same cell. To test this possibility, we have constructed two AAV vectors, each contains cDNA encoding half of the CFTR molecules. The first half (N-terminal) of cftr cDNA was constructed by inserting a stop codon downstream of the NBD1 coding region, and deletion of the downstream sequence. The second half was generated by deletion the first half of the coding region. The signal peptide and the R-domain were included in the second half. The structures of these constructs are schematically diagrammed in FIG. 8. Because each half of the coding sequence is less than 3 kb, it allowed us to express the cDNA from an AAV vector with a CMVie promoter. Functional analyses of the composite CFTR protein were done by mixing AAV vectors containing each half of the cftr at 1:1 ratio and infection of HeLa cells. The results of the patch clamp assays are shown in FIG. 9. CFTR activities that were indistinguishable from the wild type were detected in cells transduced with a mixture of AAV vectors containing both halves (N1 and C2) of the cftr cDNA. CI permeability generated by the composite CFTR was between 8.08 to 11.2 ($10^{-15}$ 1/S). These results demonstrate that a functional CFTR can be formed when the symmetrical halves of the CFTR are expressed separately in the same cells.

The results of resent research have suggested that the last four amino acid residues at the C-terminus of CFTR constitute a PTZ binding domain that may interact with other cellular proteins, and may be necessary for epical surface translocation in fully differentiated airway epithelial cells. These last four amino residues have been deleted in our C-terminal deletion constructs, including 4.1C2. To restore the functions of the PTZ domain, we have reattached the last six amino residues to the C-terminus of 4.1C2 to generate 4.1C2n. The size of the 4.1C2 is within the optimal packaging range of AAV, in spite of the 18 bp increase in size.

Figure 10:
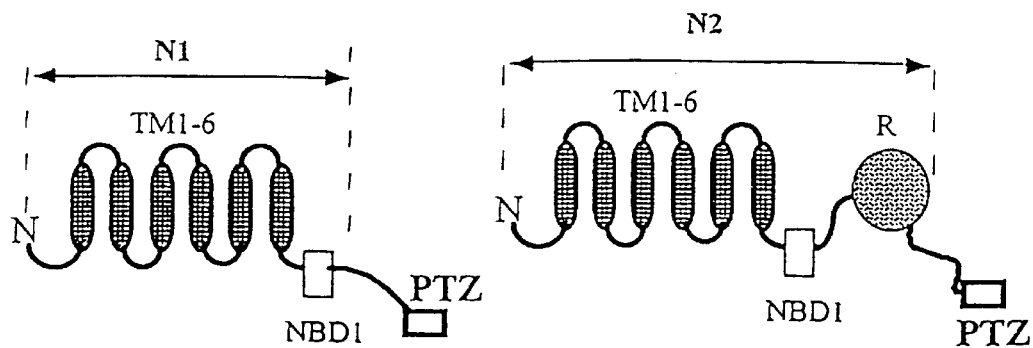
FIG. 10 shows attachment of PTZ domains to the C-termini of N1 and N2 half-CFTR constructs.

We have also applied a similar strategy to the half-CFTR pairs. In the wild-type CFTR molecule, the PTZ domain will direct the entire protein to the epical surface. In the half-CFTR pairs, the N-terminal potion may not be specifically transported to the epical surface since they do not posses the PTZ domain. To insure the epical-specific translocation of N1 and N2, we have also attached the PTZ domains to their C-termini. In both constructs, we have kept most of the loop regions to allow the free movement of the PTZ domain that is similar in the natural C-terminus of CFTR (FIG. 10).

All publications and patent applications cited in this specification are herein incorporated by reference in their entirety for all purposes as if each individual publication or patent application were specifically and individually indicated to be incorporated by reference.

What is claimed is:

1. An AAV vector comprising a transcription cassette containing a nucleic acid of interest operably linked to a promoter, an AAV ITR sequence, and which has less than about 10 non-ITR AAV nucleotides.

2. The AAV vector of claim 1, wherein the nucleic acid of interest encodes a CFTR polynucleotide.

Figure 2:
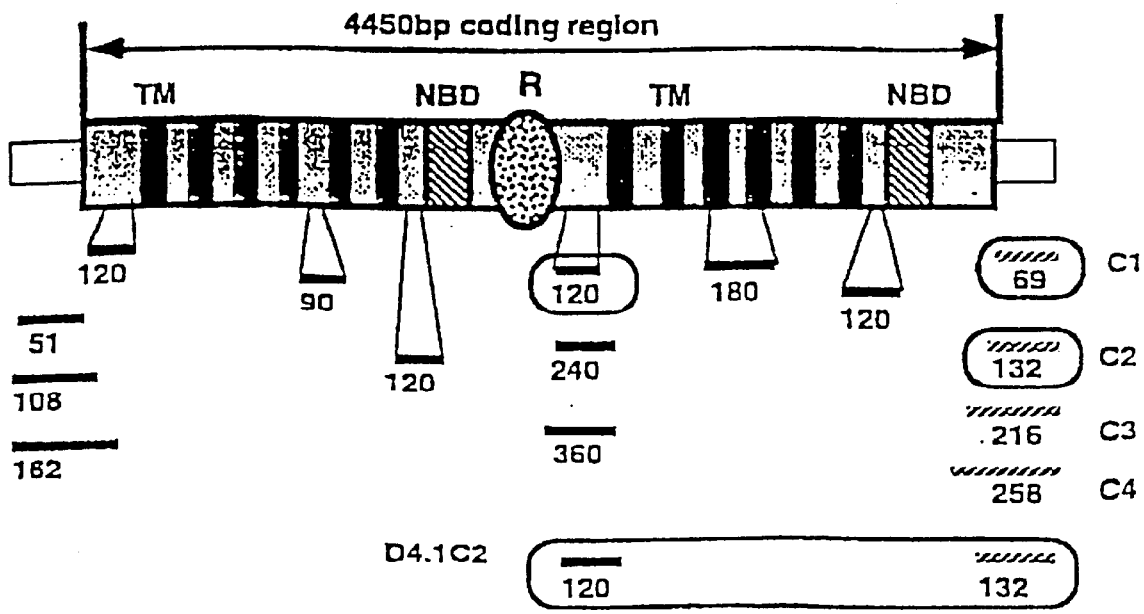
FIG. 2 shows the 16 deletions made in the CFTR gene. The CFTR gene is represented by patterned boxes. The gray regions represent loop regions, solid black boxes indicate transmembrane regions, the dotted oval represents the globular portion of the R-domain. Deletions are represented by horizontal bars. Black bars represent internal deletions, gray bars represent 5'-end truncations. Hatched bars represented 3'-end truncations. The numbers are the numbers of nucleotides deleted. The deletions that retain CFTR function are enclosed. Among the C-terminal deletions which also include the 3'-end untranslated regions, C1 contains deletion from 4503 to 4572, C2 contains deletions from 441 to 4572. C3 is not functional; it contains a deletion from 4357 to 4572. Therefore, C2 and C3 defined the border of the non-essential region that is between 4357 and 4441 bp. D4.1 contain a deletion in the flexible region of the R domain, between 2521 to 2646 nt. D4.1 C2 contain combined deletions of D4.1 and C2 (2521–2646 and 4441–4572). All these deletion mutations are functional in chloride-ion transport and therefore indicate the general regions that are non-essential for CFTR function. Although the exact nucleotide to be deleted may vary, deletions in these regions reduce the size of the CFTR coding sequence and allow the insertion of transcriptional elements into AAV to enhance the expression of CFTR gene.
Figure 3:
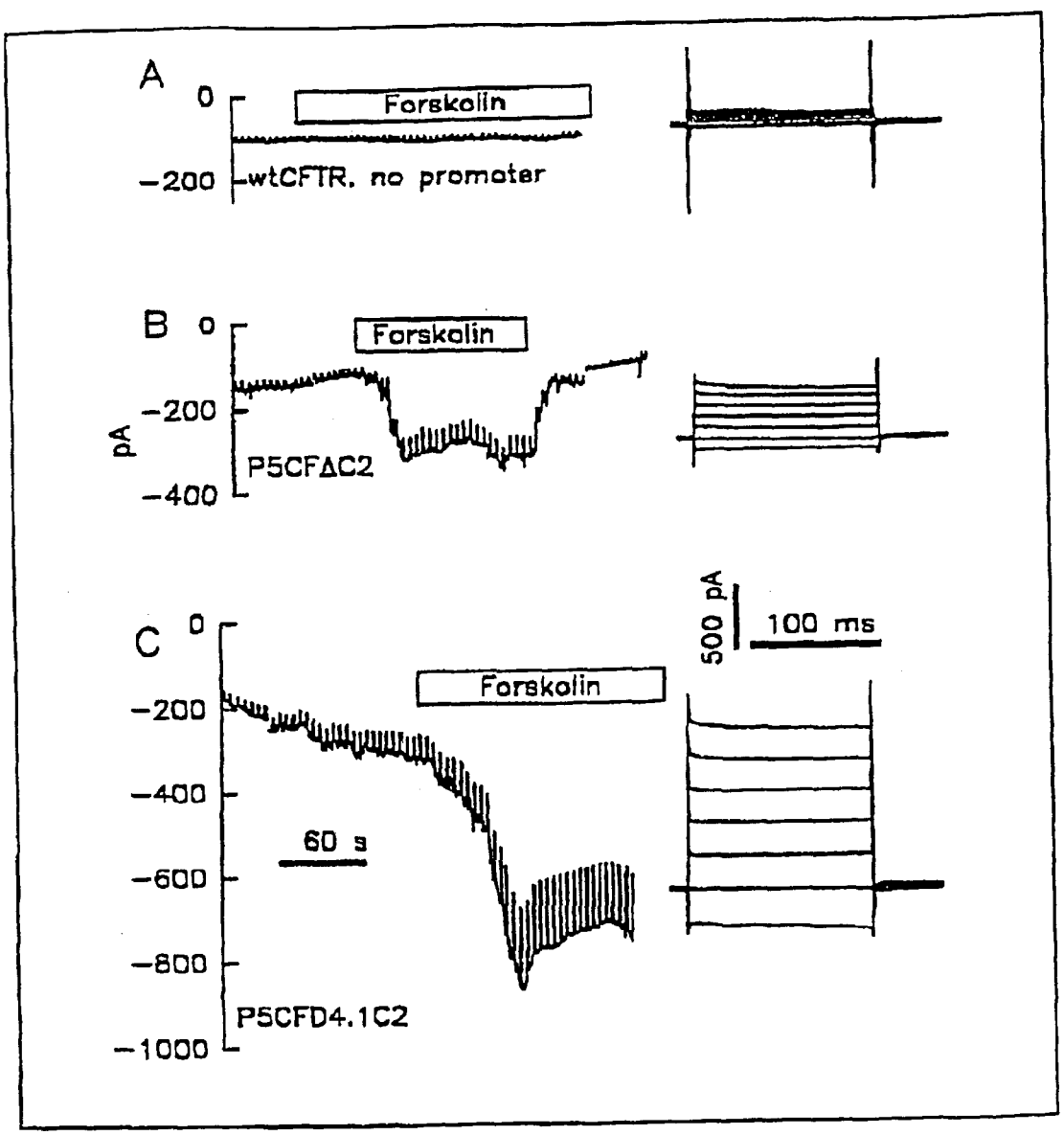
FIG. 3(Parts A–C) shows a functional analysis of short forms of CFTR gene delivered by AAV vectors. Patch clamp analysis of cells transduced with AAV-CFTR vector, in which the wild-type CFTR gene is expressed from the ITR sequences, did not show noticeable chloride channel activity (panel A). The current recording appeared as a straight line (Panel A, left graft). The recording of current/voltage (I/V) relation, shown at the right, also showed minimal CFTR activity. In contrast, a strong current (downward curve) was recorded in cells transduced with AAV-P5CF_C2, an AAV vector that contains a C-terminal deleted CFTR gene driven by the P5 promoter. This indicate the transfer of CFTR activity by the AAV vector. The recording of I/V relation (right graft) also showed a CFTR channel activity. An even stronger CFTR activity was recorded in cells transduced with AAV-P5CFD4.1C2, which contains the CFTR gene with combined R-domain and C-terminal deletions. This indicates that the AAV-P5CFD4.1C2 vector is even more efficient in transferring the CFTR function into target cells, because it is even smaller than AAV-P5CF_C2.

3. The AAV vector of claim 2, wherein the CFTR polynucleotide encodes a functional CFTR polypeptide and has one or more deletions, as shown in FIG. 2, that retain CFTR function.

4. An expression cassette comprising a truncated CFTR polynucleotide encoding a functional CFTR polypeptide, wherein said polynucleotide is operably linked to a promoter and has a deletion in the cytoplasmic tail domain or the regulatory domain.

5. The expression cassette of claim 4, wherein the CFTR polynucleotide is as shown in FIG. 2.

6. The expression cassette of claim 4, wherein said promoter is an AAV P5 promoter of about 150 bp.

7. The expression cassette of claim 4, wherein said promoter is a TK promoter of about 100 bp.

8. The expression cassette of claim 4, wherein said promoter is a SV40 early promoter of about 200 bp.

9. The expression cassette of claim 4, further comprising a 67 bp polyadenylation sequence from TK operably linked to said CFTR polynucleotide.

10. An AAV vector comprising the expression cassette of claim 4.

11. An AAV vector which has less than about 10 non-ITR AAV nucleotides, wherein said vector is synthesized using overlapping PCR primers that hybridize to the entire right-hand ITR region or the entire left-hand ITR region.

12. An AAV vector of claim 11, wherein said primers for the lefthand ITR comprise AAV nucleotides 1–76 and 50–145 and said primers for the right-hand ITR comprise AAV nucleotides 4535–4611 and 4585–4680.

* * * * *

UNITED STATES PATENT AND TRADEMARK OFFICE
CERTIFICATE OF CORRECTION

PATENT NO. : 6,294,379 B1
DATED : September 25, 2001
INVENTOR(S) : Jian-Yun Dong and Yuet Wai Kan It is certified that error appears in the above-identified patent and that said Letters Patent is hereby corrected as shown below:

Column 1,
Line 13, please change the paragraph under the heading:
STATEMENT AS TO RIGHTS TO INVENTIONS
MADE UNDER FEDERALLY SPONSORED
RESEARCH AND DEVELOPMENT to read as follows:

-- This invention was made with Government support under Grant Nos. DK07636, DK46177, DK47766 and HL46177 awarded by the National Institutes of Health. The Government has certain rights in this invention. --

Signed and Sealed this

Eighteenth Day of June, 2002

Attest:

Attesting Officer

JAMES E. ROGAN
Director of the United States Patent and Trademark Office

SEQUENCE LISTING

```
<160> NUMBER OF SEQ ID NOS:  7

<210> SEQ ID NO 1
<211> LENGTH: 4560
<212> TYPE: DNA
<213> ORGANISM: Homo sapiens
<220> FEATURE:
<223> OTHER INFORMATION: truncated cystic fibrosis transmembrane
      conductance regulator (CFTR) polynucleotide
      encoding a functional CFTR polypeptide
<221> NAME/KEY: CDS
<222> LOCATION: (133)..(4560)

<400> SEQUENCE: 1
aattggaagc aaatgacatc acagcaggtc agagaaaaag ggttgagcgg caggcaccca       60
gagtagtagg tctttggcat taggagcttg agcccagacg gccctagcag ggaccccagc     120
gcccgagaga cc atg cag agg tcg cct ctg gaa aag gcc agc gtt gtc tcc     171
              Met Gln Arg Ser Pro Leu Glu Lys Ala Ser Val Val Ser
                1               5                  10 aaa ctt ttt ttc agc tgg acc aga cca att tgg agg aaa gga tac aga        219
Lys Leu Phe Phe Ser Trp Thr Arg Pro Ile Leu Arg Lys Gly Tyr Arg
 15                  20                  25 cag cgc ctg gaa ttg tca gac ata tac caa atc cct tct gtt gat tct        267
Gln Arg Leu Glu Leu Ser Asp Ile Tyr Gln Ile Pro Ser Val Asp Ser
 30                  35                  40                  45 gct gac aat cta tct gaa aaa ttg gaa aga gaa tgg gat aga gag ctg        315
Ala Asp Asn Leu Ser Glu Lys Leu Glu Arg Glu Trp Asp Arg Glu Leu
                 50                  55                  60 gct tca aag aaa aat cct aaa ctc att aat gcc ctt cgg cga tgt ttt        363
Ala Ser Lys Lys Asn Pro Lys Leu Ile Asn Ala Leu Arg Arg Cys Phe
             65                  70                  75 ttc tgg aga ttt atg ttc tat gga atc ttt tta tat tta ggg gaa gtc        411
Phe Trp Arg Phe Met Phe Tyr Gly Ile Phe Leu Tyr Leu Gly Glu Val
         80                  85                  90 acc aaa gca gta cag cct ctc tta ctg gga aga atc ata gct tcc tat        459
Thr Lys Ala Val Gln Pro Leu Leu Leu Gly Arg Ile Ile Ala Ser Tyr
     95                 100                 105 gac ccg gat aac aag gag gaa cgc tct atc gcg att tat cta ggc ata        507
Asp Pro Asp Asn Lys Glu Glu Arg Ser Ile Ala Ile Tyr Leu Gly Ile
110                 115                 120                 125 ggc tta tgc ctt ctc ttt att gtg agg aca ctg ctc cta cac cca gcc        555
Gly Leu Cys Leu Leu Phe Ile Val Arg Thr Leu Leu Leu His Pro Ala
                130                 135                 140 att ttt ggc ctt cat cac att gga atg cag atg aga ata gct atg ttt        603
Ile Phe Gly Leu His His Ile Gly Met Gln Met Arg Ile Ala Met Phe
            145                 150                 155 agt ttg att tat aag aag act tta aag ctg tca agc cgt gtt cta gat        651
Ser Leu Ile Tyr Lys Lys Thr Leu Lys Leu Ser Ser Arg Val Leu Asp
        160                 165                 170
```

```
aaa ata agt att gga caa ctt gtt agt ctc ctt tcc aac aac ctg aac      699
Lys Ile Ser Ile Gly Gln Leu Val Ser Leu Leu Ser Asn Asn Leu Asn
175                 180                 185 aaa ttt gat gaa gga ctt gca ttg gca cat ttc gtg tgg atc gct cct      747
Lys Phe Asp Glu Gly Leu Ala Leu Ala His Phe Val Trp Ile Ala Pro
190                 195                 200                 205 ttg caa gtg gca ctc ctc atg ggg cta atc tgg gag ttg tta cag gcg      795
Leu Gln Val Ala Leu Leu Met Gly Leu Ile Trp Glu Leu Leu Gln Ala
                    210                 215                 220 tct gcc ttc tgt gga ctt ggt ttc ctg ata gtc ctt gcc ctt ttt cag      843
Ser Ala Phe Cys Gly Leu Gly Phe Leu Ile Val Leu Ala Leu Phe Gln
                225                 230                 235 gct ggg cta ggg aga atg atg atg aag tac aga gat cag aga gct ggg      891
Ala Gly Leu Gly Arg Met Met Met Lys Tyr Arg Asp Gln Arg Ala Gly
            240                 245                 250 aag atc agt gaa aga ctt gtg att acc tca gaa atg att gaa aat atc      939
Lys Ile Ser Glu Arg Leu Val Ile Thr Ser Glu Met Ile Glu Asn Ile
        255                 260                 265 caa tct gtt aag gca tac tgc tgg gaa gaa gca atg gaa aaa atg att      987
Gln Ser Val Lys Ala Tyr Cys Trp Glu Glu Ala Met Glu Lys Met Ile
270                 275                 280                 285 gaa aac tta aga caa aca gaa ctg aaa ctg act cgg aag gca gcc tat     1035
Glu Asn Leu Arg Gln Thr Glu Leu Lys Leu Thr Arg Lys Ala Ala Tyr
                    290                 295                 300 gtg aga tac ttc aat agc tca gcc ttc ttc ttc tca ggg ttc ttt gtg     1083
Val Arg Tyr Phe Asn Ser Ser Ala Phe Phe Phe Ser Gly Phe Phe Val
                305                 310                 315 gtg ttt tta tct gtg ctt ccc tat gca cta atc aaa gga atc atc ctc     1131
Val Phe Leu Ser Val Leu Pro Tyr Ala Leu Ile Lys Gly Ile Ile Leu
                320                 325                 330 cgg aaa ata ttc acc acc atc tca ttc tgc att gtt ctg cgc atg gcg     1179
Arg Lys Ile Phe Thr Thr Ile Ser Phe Cys Ile Val Leu Arg Met Ala
335                 340                 345 gtc act cgg caa ttt ccc tgg gct gta caa aca tgg tat gac tct ctt     1227
Val Thr Arg Gln Phe Pro Trp Ala Val Gln Thr Trp Tyr Asp Ser Leu
350                 355                 360                 365 gga gca ata aac aaa ata cag gat ttc tta caa aag caa gaa tat aag     1275
Gly Ala Ile Asn Lys Ile Gln Asp Phe Leu Gln Lys Gln Glu Tyr Lys
                370                 375                 380 aca ttg gaa tat aac tta acg act aca gaa gta gtg atg gag aat gta     1323
Thr Leu Glu Tyr Asn Leu Thr Thr Thr Glu Val Val Met Glu Asn Val
                385                 390                 395 aca gcc ttc tgg gag gag gga ttt ggg gaa tta ttt gag aaa gca aaa     1371
Thr Ala Phe Trp Glu Glu Gly Phe Gly Glu Leu Phe Glu Lys Ala Lys
            400                 405                 410 caa aac aat aac aat aga aaa act tct aat ggt gat gac agc ctc ttc     1419
Gln Asn Asn Asn Asn Arg Lys Thr Ser Asn Gly Asp Asp Ser Leu Phe
        415                 420                 425 ttc agt aat ttc tca ctt ctt ggt act cct gtc ctg aaa gat att aat     1467
Phe Ser Asn Phe Ser Leu Leu Gly Thr Pro Val Leu Lys Asp Ile Asn
430                 435                 440                 445 ttc aag ata gaa aga gga cag ttg ttg gcg gtt gct gga tcc act gga     1515
Phe Lys Ile Glu Arg Gly Gln Leu Leu Ala Val Ala Gly Ser Thr Gly
                450                 455                 460 gca ggc aag act tca ctt cta atg atg att atg gga gaa ctg gag cct     1563
Ala Gly Lys Thr Ser Leu Leu Met Met Ile Met Gly Glu Leu Glu Pro
            465                 470                 475 tca gag ggt aaa att aag cac agt gga aga att tca ttc tgt tct cag     1611
Ser Glu Gly Lys Ile Lys His Ser Gly Arg Ile Ser Phe Cys Ser Gln
        480                 485                 490
```

-continued

```
ttt tcc tgg att atg cct ggc acc att aaa gaa aat atc atc ttt ggt    1659
Phe Ser Trp Ile Met Pro Gly Thr Ile Lys Glu Asn Ile Ile Phe Gly
495                 500                 505 gtt tcc tat gat gaa tat aga tac aga agc gtc atc aaa gca tgc caa    1707
Val Ser Tyr Asp Glu Tyr Arg Tyr Arg Ser Val Ile Lys Ala Cys Gln
510                 515                 520                 525 cta gaa gag gac atc tcc aag ttt gca gag aaa gac aat ata gtt ctt    1755
Leu Glu Glu Asp Ile Ser Lys Phe Ala Glu Lys Asp Asn Ile Val Leu
            530                 535                 540 gga gaa ggt gga atc aca ctg agt gga ggt caa cga gca aga att tct    1803
Gly Glu Gly Gly Ile Thr Leu Ser Gly Gly Gln Arg Ala Arg Ile Ser
545                 550                 555 tta gca aga gca gta tac aaa gat gct gat ttg tat tta tta gac tct    1851
Leu Ala Arg Ala Val Tyr Lys Asp Ala Asp Leu Tyr Leu Leu Asp Ser
        560                 565                 570 cct ttt gga tac cta gat gtt tta aca gaa aaa gaa ata ttt gaa agc    1899
Pro Phe Gly Tyr Leu Asp Val Leu Thr Glu Lys Glu Ile Phe Glu Ser
575                 580                 585 tgt gtc tgt aaa ctg atg gct aac aaa act agg att ttg gtc act tct    1947
Cys Val Cys Lys Leu Met Ala Asn Lys Thr Arg Ile Leu Val Thr Ser
590                 595                 600                 605 aaa atg gaa cat tta aag aaa gct gac aaa ata tta att ttg aat gaa    1995
Lys Met Glu His Leu Lys Lys Ala Asp Lys Ile Leu Ile Leu Asn Glu
            610                 615                 620 ggt agc agc tat ttt tat ggg aca ttt tca gaa ctc caa aat cta cag    2043
Gly Ser Ser Tyr Phe Tyr Gly Thr Phe Ser Glu Leu Gln Asn Leu Gln
625                 630                 635 cca gac ttt agc tca aaa ctc atg gga tgt gat tct ttc gac caa ttt    2091
Pro Asp Phe Ser Ser Lys Leu Met Gly Cys Asp Ser Phe Asp Gln Phe
        640                 645                 650 agt gca gaa aga aga aat tca atc cta act gag acc tta cac cgt ttc    2139
Ser Ala Glu Arg Arg Asn Ser Ile Leu Thr Glu Thr Leu His Arg Phe
655                 660                 665 tca tta gaa gga gat gct cct gtc tcc tgg aca gaa aca aaa aaa caa    2187
Ser Leu Glu Gly Asp Ala Pro Val Ser Trp Thr Glu Thr Lys Lys Gln
670                 675                 680                 685 tct ttt aaa cag act gga gag ttt ggg gaa aaa agg aag aat tct att    2235
Ser Phe Lys Gln Thr Gly Glu Phe Gly Glu Lys Arg Lys Asn Ser Ile
            690                 695                 700 ctc aat cca atc aac tct ata cga aaa ttt tcc att gtg caa aag act    2283
Leu Asn Pro Ile Asn Ser Ile Arg Lys Phe Ser Ile Val Gln Lys Thr
        705                 710                 715 ccc tta caa atg aat ggc atc gaa gag gat tct gat gag cct tta gag    2331
Pro Leu Gln Met Asn Gly Ile Glu Glu Asp Ser Asp Glu Pro Leu Glu
720                 725                 730 aga agg ctg tcc tta gta cca gat tct gag cag gga gag gcg ata ctg    2379
Arg Arg Leu Ser Leu Val Pro Asp Ser Glu Gln Gly Glu Ala Ile Leu
735                 740                 745 cct cgc atc agc gtg atc agc act ggc ccc acg ctt cag gca cga agg    2427
Pro Arg Ile Ser Val Ile Ser Thr Gly Pro Thr Leu Gln Ala Arg Arg
750                 755                 760                 765 agg cag tct gtc ctg aac ctg atg aca cac tca gtt aac caa ggt cag    2475
Arg Gln Ser Val Leu Asn Leu Met Thr His Ser Val Asn Gln Gly Gln
            770                 775                 780 aac att cac cga aag aca aca gca tcc aca cga aaa gtg tca ctg gcc    2523
Asn Ile His Arg Lys Thr Thr Ala Ser Thr Arg Lys Val Ser Leu Ala
        785                 790                 795 cct cag gca aac ttg act gaa ctg gat ata tat tca aga agg tta tct    2571
Pro Gln Ala Asn Leu Thr Glu Leu Asp Ile Tyr Ser Arg Arg Leu Ser
800                 805                 810
```

```
caa gaa act ggc ttg gaa ata agt gaa gaa att aac gaa gaa gac tta    2619
Gln Glu Thr Gly Leu Glu Ile Ser Glu Glu Ile Asn Glu Glu Asp Leu
        815                 820                 825 aag gag tgc ctt ttt gat gat atg gag agc ata cca gca gtg act aca    2667
Lys Glu Cys Leu Phe Asp Asp Met Glu Ser Ile Pro Ala Val Thr Thr
830                 835                 840                 845 tgg aac aca tac ctt cga tat att act gtc cac aag agc tta att ttt    2715
Trp Asn Thr Tyr Leu Arg Tyr Ile Thr Val His Lys Ser Leu Ile Phe
                850                 855                 860 gtg cta att tgg tgc tta gta att ttt ctg gca gag gtg gct gct tct    2763
Val Leu Ile Trp Cys Leu Val Ile Phe Leu Ala Glu Val Ala Ala Ser
            865                 870                 875 ttg gtt gtg ctg tgg ctc ctt gga aac act cct ctt caa gac aaa ggg    2811
Leu Val Val Leu Trp Leu Leu Gly Asn Thr Pro Leu Gln Asp Lys Gly
        880                 885                 890 aat agt act cat agt aga aat aac agc tat gca gtg att atc acc agc    2859
Asn Ser Thr His Ser Arg Asn Asn Ser Tyr Ala Val Ile Ile Thr Ser
895                 900                 905 acc agt tcg tat tat gtg ttt tac att tac gtg gga gta gcc gac act    2907
Thr Ser Ser Tyr Tyr Val Phe Tyr Ile Tyr Val Gly Val Ala Asp Thr
910                 915                 920                 925 ttg ctt gct atg gga ttc ttc aga ggt cta cca ctg gtg cat act cta    2955
Leu Leu Ala Met Gly Phe Phe Arg Gly Leu Pro Leu Val His Thr Leu
                930                 935                 940 atc aca gtg tcg aaa att tta cac cac aaa atg tta cat tct gtt ctt    3003
Ile Thr Val Ser Lys Ile Leu His His Lys Met Leu His Ser Val Leu
            945                 950                 955 caa gca cct atg tca acc ctc aac acg ttg aaa gca ggt ggg att ctt    3051
Gln Ala Pro Met Ser Thr Leu Asn Thr Leu Lys Ala Gly Gly Ile Leu
        960                 965                 970 aat aga ttc tcc aaa gat ata gca att ttg gat gac ctt ctg cct ctt    3099
Asn Arg Phe Ser Lys Asp Ile Ala Ile Leu Asp Asp Leu Leu Pro Leu
975                 980                 985 acc ata ttt gac ttc atc cag ttg tta tta att gtg att gga gct ata    3147
Thr Ile Phe Asp Phe Ile Gln Leu Leu Leu Ile Val Ile Gly Ala Ile
990                 995                 1000                1005 gca gtt gtc gca gtt tta caa ccc tac atc ttt gtt gca aca gtg cca    3195
Ala Val Val Ala Val Leu Gln Pro Tyr Ile Phe Val Ala Thr Val Pro
                1010                1015                1020 gtg ata gtg gct ttt att atg ttg aga gca tat ttc ctc caa acc tca    3243
Val Ile Val Ala Phe Ile Met Leu Arg Ala Tyr Phe Leu Gln Thr Ser
            1025                1030                1035 cag caa ctc aaa caa ctg gaa tct gaa ggc agg agt cca att ttc act    3291
Gln Gln Leu Lys Gln Leu Glu Ser Glu Gly Arg Ser Pro Ile Phe Thr
        1040                1045                1050 cat ctt gtt aca agc tta aaa gga cta tgg aca ctt cgt gcc ttc gga    3339
His Leu Val Thr Ser Leu Lys Gly Leu Trp Thr Leu Arg Ala Phe Gly
    1055                1060                1065 cgg cag cct tac ttt gaa act ctg ttc cac aaa gct ctg aat tta cat    3387
Arg Gln Pro Tyr Phe Glu Thr Leu Phe His Lys Ala Leu Asn Leu His
1070                1075                1080                1085 act gcc aac tgg ttc ttg tac ctg tca aca ctg cgc tgg ttc caa atg    3435
Thr Ala Asn Trp Phe Leu Tyr Leu Ser Thr Leu Arg Trp Phe Gln Met
                1090                1095                1100 aga ata gaa atg att ttt gtc atc ttc ttc att gct gtt acc ttc att    3483
Arg Ile Glu Met Ile Phe Val Ile Phe Phe Ile Ala Val Thr Phe Ile
            1105                1110                1115 tcc att tta aca aca gga gaa gga gaa gga aga gtt ggt att atc ctg    3531
Ser Ile Leu Thr Thr Gly Glu Gly Glu Gly Arg Val Gly Ile Ile Leu
        1120                1125                1130
```

```
                                                         -continued act tta gcc atg aat atc atg agt aca ttg cag tgg gct gta aac tcc      3579
Thr Leu Ala Met Asn Ile Met Ser Thr Leu Gln Trp Ala Val Asn Ser
    1135                1140                1145 agc ata gat gtg gat agc ttg atg cga tct gtg agc cga gtc ttt aag      3627
Ser Ile Asp Val Asp Ser Leu Met Arg Ser Val Ser Arg Val Phe Lys
1150                1155                1160                1165 ttc att gac atg cca aca gaa ggt aaa cct acc aag tca acc aaa cca      3675
Phe Ile Asp Met Pro Thr Glu Gly Lys Pro Thr Lys Ser Thr Lys Pro
                1170                1175                1180 tac aag aat ggc caa ctc tcg aaa gtt atg att att gag aat tca cac      3723
Tyr Lys Asn Gly Gln Leu Ser Lys Val Met Ile Ile Glu Asn Ser His
            1185                1190                1195 gtg aag aaa gat gac atc tgg ccc tca ggg ggc caa atg act gtc aaa      3771
Val Lys Lys Asp Asp Ile Trp Pro Ser Gly Gly Gln Met Thr Val Lys
        1200                1205                1210 gat ctc aca gca aaa tac aca gaa ggt gga aat gcc ata tta gag aac      3819
Asp Leu Thr Ala Lys Tyr Thr Glu Gly Gly Asn Ala Ile Leu Glu Asn
    1215                1220                1225 att tcc ttc tca ata agt cct ggc cag agg gtg ggc ctc ttg gga aga      3867
Ile Ser Phe Ser Ile Ser Pro Gly Gln Arg Val Gly Leu Leu Gly Arg
1230                1235                1240                1245 act gga tca ggg aag agt act ttg tta tca gct ttt ttg aga cta ctg      3915
Thr Gly Ser Gly Lys Ser Thr Leu Leu Ser Ala Phe Leu Arg Leu Leu
                1250                1255                1260 aac act gaa gga gaa atc cag atc gat ggt gtg tct tgg gat tca ata      3963
Asn Thr Glu Gly Glu Ile Gln Ile Asp Gly Val Ser Trp Asp Ser Ile
            1265                1270                1275 act ttg caa cag tgg agg aaa gcc ttt gga gtg ata cca cag aaa gta      4011
Thr Leu Gln Gln Trp Arg Lys Ala Phe Gly Val Ile Pro Gln Lys Val
        1280                1285                1290 ttt att ttt tct gga aca ttt aga aaa aac ttg gat ccc tat gaa cag      4059
Phe Ile Phe Ser Gly Thr Phe Arg Lys Asn Leu Asp Pro Tyr Glu Gln
    1295                1300                1305 tgg agt gat caa gaa ata tgg aaa gtt gca gat gag gtt ggg ctc aga      4107
Trp Ser Asp Gln Glu Ile Trp Lys Val Ala Asp Glu Val Gly Leu Arg
1310                1315                1320                1325 tct gtg ata gaa cag ttt cct ggg aag ctt gac ttt gtc ctt gtg gat      4155
Ser Val Ile Glu Gln Phe Pro Gly Lys Leu Asp Phe Val Leu Val Asp
                1330                1335                1340 ggg ggc tgt gtc cta agc cat ggc cac aag cag ttg atg tgc ttg gct      4203
Gly Gly Cys Val Leu Ser His Gly His Lys Gln Leu Met Cys Leu Ala
            1345                1350                1355 aga tct gtt ctc agt aag gcg aag atc ttg ctg ctt gat gaa ccc agt      4251
Arg Ser Val Leu Ser Lys Ala Lys Ile Leu Leu Leu Asp Glu Pro Ser
        1360                1365                1370 gct cat ttg gat cca gta aca tac caa ata att aga aga act cta aaa      4299
Ala His Leu Asp Pro Val Thr Tyr Gln Ile Ile Arg Arg Thr Leu Lys
    1375                1380                1385 caa gca ttt gct gat tgc aca gta att ctc tgt gaa cac agg ata gaa      4347
Gln Ala Phe Ala Asp Cys Thr Val Ile Leu Cys Glu His Arg Ile Glu
1390                1395                1400                1405 gca atg ctg gaa tgc caa caa ttt ttg gtc ata gaa gag aac aaa gtg      4395
Ala Met Leu Glu Cys Gln Gln Phe Leu Val Ile Glu Glu Asn Lys Val
                1410                1415                1420 cgg cag tac gat tcc atc cag aaa ctg ctg aac gag agg agc ctc ttc      4443
Arg Gln Tyr Asp Ser Ile Gln Lys Leu Leu Asn Glu Arg Ser Leu Phe
            1425                1430                1435 cgg caa gcc atc agc ccc tcc gac agg gtg aag ctc ttt ccc cac cgg      4491
Arg Gln Ala Ile Ser Pro Ser Asp Arg Val Lys Leu Phe Pro His Arg
        1440                1445                1450
```

```
aac tca agc aag tgc aag tct aag ccc cag att gct gct ctg aaa gag    4539
Asn Ser Ser Lys Cys Lys Ser Lys Pro Gln Ile Ala Ala Leu Lys Glu
    1455                1460                1465 gag aca gaa gaa gag gtg caa                                         4560
Glu Thr Glu Glu Glu Val Gln
1470                1475

<210> SEQ ID NO 2
<211> LENGTH: 1476
<212> TYPE: PRT
<213> ORGANISM: Homo sapiens
<223> OTHER INFORMATION: truncated cystic fibrosis transmembrane

<400> SEQUENCE: 2

Met Gln Arg Ser Pro Leu Glu Lys Ala Ser Val Val Ser Lys Leu Phe
  1               5                  10                  15

Phe Ser Trp Thr Arg Pro Ile Leu Arg Lys Gly Tyr Arg Gln Arg Leu
                 20                  25                  30

Glu Leu Ser Asp Ile Tyr Gln Ile Pro Ser Val Asp Ser Ala Asp Asn
             35                  40                  45

Leu Ser Glu Lys Leu Glu Arg Glu Trp Asp Arg Glu Leu Ala Ser Lys
         50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
        130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
        210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
        290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335
```

-continued

```
Phe Thr Thr Ile Ser Phe Cys Ile Val Leu Arg Met Ala Val Thr Arg
        340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
        370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
        450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
        530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu Asn Glu Gly Ser Ser
        610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
        690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750
```

```
Ser Val Ile Ser Thr Gly Pro Thr Leu Gln Ala Arg Arg Gln Ser
    755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
                820                 825                 830

Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
                900                 905                 910

Tyr Tyr Val Phe Tyr Ile Tyr Val Gly Val Ala Asp Thr Leu Leu Ala
                915                 920                 925

Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
                1060                1065                1070

Tyr Phe Glu Thr Leu Phe His Lys Ala Leu Asn Leu His Thr Ala Asn
    1075                1080                1085

Trp Phe Leu Tyr Leu Ser Thr Leu Arg Trp Phe Gln Met Arg Ile Glu
    1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
            1125                1130                1135

Met Asn Ile Met Ser Thr Leu Gln Trp Ala Val Asn Ser Ser Ile Asp
        1140                1145                1150

Val Asp Ser Leu Met Arg Ser Val Ser Arg Val Phe Lys Phe Ile Asp
    1155                1160                1165
```

-continued

```
Met Pro Thr Glu Gly Lys Pro Thr Lys Ser Thr Lys Pro Tyr Lys Asn
    1170                1175                1180
Gly Gln Leu Ser Lys Val Met Ile Ile Glu Asn Ser His Val Lys Lys
1185                1190                1195                1200
Asp Asp Ile Trp Pro Ser Gly Gln Met Thr Val Lys Asp Leu Thr
            1205                1210                1215
Ala Lys Tyr Thr Glu Gly Gly Asn Ala Ile Leu Glu Asn Ile Ser Phe
            1220                1225                1230
Ser Ile Ser Pro Gly Gln Arg Val Gly Leu Leu Gly Arg Thr Gly Ser
            1235                1240                1245
Gly Lys Ser Thr Leu Leu Ser Ala Phe Leu Arg Leu Leu Asn Thr Glu
    1250                1255                1260
Gly Glu Ile Gln Ile Asp Gly Val Ser Trp Asp Ser Ile Thr Leu Gln
1265                1270                1275                1280
Gln Trp Arg Lys Ala Phe Gly Val Ile Pro Gln Lys Val Phe Ile Phe
            1285                1290                1295
Ser Gly Thr Phe Arg Lys Asn Leu Asp Pro Tyr Glu Gln Trp Ser Asp
            1300                1305                1310
Gln Glu Ile Trp Lys Val Ala Asp Glu Val Gly Leu Arg Ser Val Ile
            1315                1320                1325
Glu Gln Phe Pro Gly Lys Leu Asp Phe Val Leu Val Asp Gly Gly Cys
    1330                1335                1340
Val Leu Ser His Gly His Lys Gln Leu Met Cys Leu Ala Arg Ser Val
1345                1350                1355                1360
Leu Ser Lys Ala Lys Ile Leu Leu Leu Asp Glu Pro Ser Ala His Leu
            1365                1370                1375
Asp Pro Val Thr Tyr Gln Ile Ile Arg Arg Thr Leu Lys Gln Ala Phe
            1380                1385                1390
Ala Asp Cys Thr Val Ile Leu Cys Glu His Arg Ile Glu Ala Met Leu
            1395                1400                1405
Glu Cys Gln Gln Phe Leu Val Ile Glu Glu Asn Lys Val Arg Gln Tyr
    1410                1415                1420
Asp Ser Ile Gln Lys Leu Leu Asn Glu Arg Ser Leu Phe Arg Gln Ala
1425                1430                1435                1440
Ile Ser Pro Ser Asp Arg Val Lys Leu Phe Pro His Arg Asn Ser Ser
            1445                1450                1455
Lys Cys Lys Ser Lys Pro Gln Ile Ala Ala Leu Lys Glu Thr Glu
            1460                1465                1470
Glu Glu Val Gln
        1475
```

```
<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:synthetic
      short polyadenylation signal

<400> SEQUENCE: 3
ctcgagaata aagtcgac                                                 18

<210> SEQ ID NO 4
<211> LENGTH: 54
<212> TYPE: DNA
<213> ORGANISM: Artificial Sequence
<220> FEATURE:
```

-continued

```
<223> OTHER INFORMATION: Description of Artificial Sequence:short
      polyadenylation signal with four AATAAA repeats

<400> SEQUENCE: 4
ctcgagaata aactcgagaa taaactcgag aataaactcg agaataaagt cgac        54

<210> SEQ ID NO 5
<211> LENGTH: 67
<212> TYPE: DNA
<213> ORGANISM: Artificial Sequence
<220> FEATURE:
<223> OTHER INFORMATION: Description of Artificial Sequence:short
      polyadenylation signal of the TK gene of Herpes
      simplex virus (HSV) truncated to 67 bp

<400> SEQUENCE: 5
ctcgagctat gacggcaata aaaagacaga ataaaacgca cgggtgttgg gtcgtttgtt        60
cgtcgac        67

<210> SEQ ID NO 6
<211> LENGTH: 200
<212> TYPE: DNA
<213> ORGANISM: Artificial Sequence
<220> FEATURE:
<223> OTHER INFORMATION: Description of Artificial Sequence:HSV-TK
      promoter

<400> SEQUENCE: 6
aagaaaatat atttgcatgt ctttagttct atgatgacac aaacccgcc cagcgtcttg        60 tcattggcga attcgaacac gcagatgcag tcggggcggc gcggtcccag gtccacttcg       120
catattaagg tgacgcgtgt ggcctcgaac accgagcgac cctgcagcga cccgcttaac       180
agcgtcaaca gcgtgccgca       200

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:poly purine
      tract

<400> SEQUENCE: 7
gggtgttggg tcgtttgtt        19
```